United States Patent [19]
Foresta et al.

[11] Patent Number: 5,591,777
[45] Date of Patent: Jan. 7, 1997

[54] USE OF 6,7-SUBSTITUTED-2-AMINOTETRALINES FOR PREPARING PHARMACEUTICAL COMPOSITIONS USEFUL FOR THE TREATMENT OF SEPTIC SHOCK, AND ANTIPYRETIC AND ANTIINFLAMMATORY PHARMACEUTICAL COMPOSITIONS

[75] Inventors: Piero Foresta, Pomezia; Vito Ruggiero, Rome, both of Italy

[73] Assignee: Sigma-Tau Industrie Farmaceutiche Riunite S.p.A., Rome, Italy

[21] Appl. No.: 607,452

[22] Filed: Feb. 27, 1996

[30] Foreign Application Priority Data

Mar. 9, 1995 [IT] Italy .................. RM95A0143

[51] Int. Cl.$^6$ .................. A61K 31/135
[52] U.S. Cl. .......... 514/653; 514/654; 514/657
[58] Field of Search .................. 514/653, 654, 514/657

[56] References Cited

U.S. PATENT DOCUMENTS 5,047,433  9/1991  Marzi et al. .................. 514/653
5,376,687  12/1994  Hacksell et al. .................. 514/657

OTHER PUBLICATIONS

Chem. Abst. 109:149106, Mauro et al. 1988.
Chem. Abst. 115:92956, Marzi et al. 1991.
Chem. Abst. 116:235268, Foresta et al. 1992.

*Primary Examiner*—Raymond Henley, III
*Attorney, Agent, or Firm*—Oblon, Spivak, McClelland, Maier & Neustadt, P.C.

[57] ABSTRACT

The use of 6,7-substituted-2-aminotetralines (e.g. 2-amino-6-fluoro-7-methoxytetraline) is disclosed for preparing pharmaceutical compositions useful for the treatment of septic shock and having antiinflammatory and antipyretic activities.

8 Claims, No Drawings

USE OF 6,7-SUBSTITUTED-2-AMINOTETRALINES FOR PREPARING PHARMACEUTICAL COMPOSITIONS USEFUL FOR THE TREATMENT OF SEPTIC SHOCK, AND ANTIPYRETIC AND ANTIINFLAMMATORY PHARMACEUTICAL COMPOSITIONS

The present invention relates to the use of 6,7-substituted-2-aminotetralines and of their pharmacologically acceptable salts for preparing pharmaceutical compositions useful for the treatment of septic shock and pharmaceutical compositions having antiinflammatory and antipyretic activity.

These 6,7-substituted-2-aminotetralines have general formula (I):

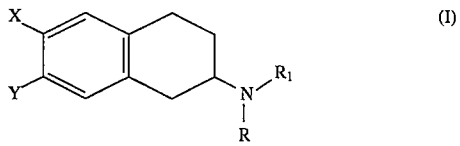

wherein X and Y, equal or different, are selected from the group consisting of methoxy, acetoxy and fluorine and R and $R_1$, equal or different, are selected from the group consisting of hydrogen, ethyl, propyl, cyclopropylmethyl, 2-phenyl-2-hydroxyethyl, 2-hydroxy-2-(4-methylphenyl)ethyl and 2-hydroxy-3-(4-methoxyphenoxy)propyl.

Among the 6,7-substituted-2-aminotetralines of formula (I) the following compounds are particularly preferred wherein:

(1) X=Y=methoxy; R=hydrogen, $R_1$=2-hydroxy(4-methylphenyl)ethyl:

2-[(N-2-hydroxy-2-(4-methylphenyl)ethyl)amino]-6,7-dimethoxytetraline. (hereinafter: ST 563);

(2) X=Y=methoxy; R=ethyl; $R_1$=2=phenyl-2-hydroxyethyl:

2-[(N-ethyl, N-2-phenyl-2-hydroxyethyl)amino]-6,7-dimethoxytetraline. (hereinafter: ST 570);

(3) X=Y=methoxy; R=$R_1$=cyclopropylmethyl:

2-[N,N-dicyclopropylmethyl)amino]-6,7-dimethoxytetraline. (hereinafter: ST 557);

(4) X=Y=methoxy; R=hydrogen, $R_1$=2=hydroxy-3-(4-methoxyphenoxy) propyl:

2-[N-2-hydroxy-3-(4-methoxyphenoxy)propyl)amino]-6,7-dimethoxytetraline. (hereinafter: ST 564);

(5) X=fluorine, Y=methoxy; R=R1=hydrogen:

2-amino-6-fluoro-7-methoxytetraline. (hereinafter: ST 626); and (6) X=Y=acethoxy; R=hydrogen, R1=propyl:

2-N-propylamino-6,7-diacethoxytetraline. (hereinafter: ST 608).

The 6,7-substituted-2-aminotetralines of formula (I) and the compounds (1)-(6) particularly, are known compounds.

Indeed, the Italian patent 1241988 or the corresponding EP-A-0466662 disclose pharmaceutical compositions having immunomodulating activity, which contain such aminotetralines as active ingredients.

Even before, the antihypertensive activity of ST 563 and ST 570 had been disclosed in EP-B-0273017.

Also, the antihypertensive activity of compounds such as ST 557, ST 564 and ST 626 had been disclosed already in the Italian patents 1219428 and 1224243 and in J. Med. Chem. 29, 1615 (1986), respectively.

It is apparent that there is no relationship at all between the already known immunomodulating and antihypertensive activity of the aminotetralines of formula (I) and the therapeutical activity against septic shock and as an antiinflammatory and antipyretic drugs firstly disclosed herein.

Septic shock is a clinical syndrome associated with a high mortality rate and characterized by various haemodynamic, immunological and biochemical abnormalities.

Its increasing incidence places it among the most serious nosocomial pathologies, especially in intensive care units, despite the use of a variety of antibiotics, surgical drainage, intervention with vasoactive substances and metabolic support. It is estimated that approximately 100.000 people die of endotoxic shock every year in the USA.

The main cause of this type of pathology is a severe infection with Gram-negative bacteria, whose physio-pathological effects are ascribable to LPS, a component of the outer layer of the bacterial membrane capable of causing septic shock by interacting with various components of the host's immune system, particularly macrophages.

This immunocompetent cell population, in fact, releases different endogenous mediators which prove ultimately responsible for the complex pathological picture which ensues.

The fatal outcome of septic shock in man has recently been linked to the systemic release of substancial mounts of various cytokines.

There are, in fact, numerous studies which show that an abnormal modulation of cytokines such as IL-1. IL-6, TNF and IFN-$\gamma$ is closely related to a severe septic shock.

Other inflammation mediators (PAF, LTD, BK, substance P) would also appear to be involved in the septic physiopathology.

TNF (Tumor Necrosis Factor) is in any event the cytokine which plays a crucial role as mediator in the host's response to LPS (Tracery K. J., Tumor Necrosis Factor (Cachectin) in the Biology of Endotoxic Shock Syndrome. *Circ. Shock* 1991; 35: 123–28), since its involvement has been demonstrated in various metabolic abnormalities characterizing the course of shock (Starnes H. K., Warren R. S., Jeevandam M. et al. Tumor Necrosis Factor and the acute metabolic response to tissue injury in man. *J. Clin, Invest.* 1988: 82:1321), the negative prognosis of which is often related to excessively high serum concentrations of TNF (Dames P., Reuter A., Gysen P., Demonty J., Lamy M., Franchimont P. Tumor Necrosis Factor and interleukin-1 serum levels during severe sepsis in humans. *Crit. Care Mad.* 1989; 17:975–978. Debets J. M. H., Kampmeijer R., Van Der Linden MPMH., Buurman W. A., Van Der Linden C. J., Plasma Tumor Necrosis Factor and mortality in critically ill septic patients. *Crit. Care Med.* 1989; 17:489–494).

In fact, high level of TNF are found in the serum of animals experimentally intoxicated with LPS, and animals directly inoculated with TNF develop a toxic syndrome which is indistinguishable from endotoxinaemia (Natanson C., Eichnols P. W., Danner R. L., Endotoxin and Tumor Nevrosis Factor challenges in dogs simulate the cardiovascular profile of human septic shock. J. Exp. Med. 1989; 169:823–832. Beutler B. Milsak I. W., Cerami A., Passive immunization against cachectin/Tumor Necrosis Factor protects mice from lethal effect of endotoxin. Science 1985: 229:869–871).

Consequently, compounds which block or antagonize TNF may be regarded as useful therapeutical candidates in the treatment of septic shock.

Evaluation of the effect of ST 626 on the lethality induced by Lipopolysaccharide (LPS from *E. coli* 026:B6) in BALB/c mice Animals Male BALB/c inbred mice (Iffa Credo) aged approx. 7 weeks have been utilized (8 animals per experimental group).

Experimental procedure

The compound ST 626, solubilized in sterile saline, was administered orally at the dose of 50 mg/kg b.w. following 2 different treatment schedules, namely 1) at −60' and +5', and 2) at +5' and +120' with respect to the LPS injection. The LPS utilized (from E. coli O26:B6) was first solubilized in sterile saline and then injected intraperitoneally at the dose of 15 mg/kg in a volume of 0.1 ml per 10 gr of body weight (b.w.). Survival was assessed daily for 10 days following LPS challenge.

Results

The overall results obtained with ST 626 in this model of endotoxic shock, which was based on a double oral administration of the compound either at −60' and +5' or at +5' and +120' with respect to the LPS challenge, are reported in Table 1. It can be noticed that ST 626 is able to greatly reduce the LPS-induced lethality, though this effect is not statistically significant. Besides, while LPS control animals died within 2 days after the challenge, both animals of each ST 626-treated group died 6 days after the LPS challenge.

TABLE 1

Effect of oral ST 626 administrations (50 mg/kg) on the lethality induced in mice[a] by LPS (from E. coli O26:B6) injection.

| Experimental group | Treatment[b] | Lethality D/T[c] | Survival (%) |
|---|---|---|---|
| LPS | — | 6/8 | 25 |
| ST 626 | −60' and +5' | 2/8 | 75 |
| ST 626 | +5' and +120' | 2/8 | 75 |

[a] = BALB/c mice.
[b] = Time of ST 626 administration with respect to the LPS challenge.
[c] = Dead/Total in each experimental group.

Evaluation of the effect of ST 626 on the lethality induced by Lipopolysaccharide (LPS from E. coli 055:B5) in C57BL/6 mice Animals Male C57BL/6 inbred mice (Iffa Credo) aged approx. 7 weeks have been utilized (7–8 animals per experimental group).

Experimental procedure

The compound ST 626, solubilized in sterile saline, was administered orally at the dose of 50 mg/kg b.w. following 2 different treatment schedules, namely 1) at −60' and +5', and 2) at +5' and +120' with respect to the LPS injection. The LPS utilized (from E. coli 055:B5) was first solubilized in sterile saline and then injected intraperitoneally at the dose of 45 mg/kg in a volume of 0.1 ml per 10 gr of body weight (b.w.). Survival was assessed daily for 10 days following LPS challenge.

Results

The data reported in Table 2 show a complete protective effect of ST 626 (p<0.02) when administered twice orally at −60' and +5' with respect to the LPS challenge. The double oral treatment with ST 626 administered after the challenge (at +5' and +120') is not quite so effective (57% survival vs. 12.5% of LPS control group). However, the Mean Survival Time (MST) value of the ST 626-treated group (MST>10 days) is statistically significant (p<0.01) with respect to the control group (MST=3 days).

TABLE 2

Effect of oral ST 626 administrations (50 mg/kg) on the lethality induced in mice[a] by LPS (from E. coli O55:B5) injection.

| Experimental group | Treatment[b] | Lethality D/T[c] | Survival (%) |
|---|---|---|---|
| LPS | — | 7/8 | 12.5 |
| ST 626 | −60' and +5' | 0/7* | 100 |
| ST 626 | +5' and +120' | 3/7 | 57.2 |

[a] = C57BL/6 mice.
[b] = Time of ST 626 administration with respect to the LPS challenge.
[c] = Dead/Total in each experimental group.
* = Fisher exact test: $p < 0.01$.

Evaluation of the effect of ST 626 on the lethality induced by Lipopolysaccharide (LPS from E. coli 055:B5) in C57BL/6 mice after sensitization with D-galactosamine.

Animals

Male C57BL/6 inbred mice (Iffa Credo) aged approx. 7 weeks have been utilized (8 animals per experimental group).

Experimental procedure

The compound ST 626. solubilized in sterile saline, was administered orally at the dose of 50 mg/kg b.w. following 2 different treatment schedules, namely 1) at −60' and +5', and 2) at +5' and +120' with respect to the LPS injection. The LPS utilized (from E. coli 055:B5) was first solubilized in sterile saline and then injected intraperitoneally at the dose of 0.01 mg/kg in D-galactosamine-pretreated animals. The sensitizing compound was injected i.v. at the dose of 1000 mg/kg, 30 minutes prior to LPS challenge. Survival was assessed daily for 10 days following LPS challenge.

Results

A complete protection (100% survival) was obtained with ST 626 in this model of endotoxic shock in mice sensitized with D-galactosamine (Table 3). Most interestingly, ST 626 appears to be effective even when administered after the LPS challenge.

TABLE 3

Effect of oral ST 626 administrations (50 mg/kg) on the lethality induced in mice[a] by LPS (from E. coli O55:B5) after sensitization with D-galactosamine.

| Experimental group | Treatment[b] | Lethality D/T[c] | Survival (%) |
|---|---|---|---|
| D-galactosamine + LPS | — | 7/8 | 12.5 |
| ST 626 | −60' and +5' | 0/8* | 100 |
| ST 626 | +5' and +120' | 0/8* | 100 |

[a] = C57BL/6 mice.
[b] = Time of ST 626 administration with respect to the LPS challenge.
[c] = Dead/Total in each experimental group.
* = Fisher exact test: $p < 0.01$.

Evaluation of the effect of ST 626 on serum TNF (Tumor Necrosis Factor) levels induced by LPS in mice.

Animals

Male BALB/c inbred mice (Iffa Credo) aged approx. 8 weeks have been utilized (8 animals per experimental group).

Experimental Procedure

The compound ST 626 was administered orally at the dose of 100 mg/kg at 90 minutes prior to the LPS challenge. The animals were then treated with LPS (from E. coli 026:B6) at the dose of 10 mg/kg i.p. $CO_2$-anesthetized mice were bled by retro-orbital sinus puncture taking blood samples 1 h following LPS injection, i.e. when TNF reached its peak levels.

To test whether ST 626 was able per se to induce detectable levels of the cytokine under investigation, two groups of 4 animals each were treated with ST 626 alone, administered orally either at 60' or 120' prior to blood sampling. Blood samples were all allowed to clot at room temperature to separate serum, which was then centrifuged. Serum samples were stored at −80° C. until assayed. TNF biological activity in serum was determined by using the L929 cell line (a murine fibrosarcoma), which is very sensitive to the TNF cytotoxic activity (for details see V. Ruggiero, C. Chiapparino, S. Manganello, L. Pacello, P. Foresta & E. Arrigoni Martelli. *Beneficial Effects of a Novel Platelet-Activating Factor Receptor Antagonist, ST 899, on Endotoxin-Induced Shock in Mice*, SHOCK, 2, n° 4, pages 275–280, 1994). The TNF activity in serum is expressed as Biological Units/ml.

Results

The compound ST 626, administered orally at the dose of 100 mg/kg at 90 minutes prior to the LPS challenge, significantly ($p<0.001$) reduces serum TNF levels induced by LPS, and is not able to elicit TNF production when administered in control mice (Table 4).

TABLE 4

Effect of ST 626[a] on serum TNF peak levels (1 h post LPS) in control and LPS-treated[b] mice[c].
Data are expressed as mean values (8 animals) ± S. E..

| | TNF (U/ml) | | | | |
|---|---|---|---|---|---|
| | Control | ST 626 (−60') | ST 626 (−120') | LPS | LPS + ST 626 |
| Mean | 2.50 | 1.23 | 0.60 | 89.77 | 3.33 |
| ± S. E. | 1.02 | 0.63 | 0.28 | 19.65 | 0.76 |
| P | | ns. | n.s. | <0.001 | <0.001 |

[a] = The substance was administered orally at the dose of 100 mg/kg at −60' or −120' in control mice and at −90' in LPS-treated mice.
[b] = LPS from *E. coli* O26:B6.
[c] = BALB/c mice.
* = Student "t" test (ST 626 vs. control; LPS vs. control; LPS + ST 626 vs. LPS).

Evaluation of the effect of ST 626 on serum TNF-α (Tumor Necrosis Factor) levels induced by LPS in mice.

Animals

Male BALB/c inbred mice (Iffa Credo) aged approx. 8 weeks have been utilized (8 animals per experimental group).

Experimental Procedure The compound ST 626 was administered orally at the dose of 50 mg/kg either at 60 minutes before and again 5 minutes after the LPS challenge or only 5 minutes after LPS. The animals were i.p. treated with LPS (from *E. coli* O26:B6), solubilized in sterile saline, at the dose of 10 mg/kg. $CO_2$-anesthetized mice were bled by retro-orbital sinus puncture taking blood samples 1 h following LPS injection, i.e. when TNF reached its serum peak levels.

Blood samples were all allowed to clot at room temperature for 30' to separate serum, which was then centrifuged (30' at 2000 rpm). The TNF-α serum concentrations were determined by using the commercially available ELISA kit for murine TNF-α (Genzyme, Boston, Mass.) and following the manufacturer's instructions.

Results

The increased TNF-α serum levels, which follow LPS injection, almost disappear (Table 5) after the double administration of ST 626 (50 mg/kg os at −60' and again at +5', with respect to LPS). Most notably, the single administration of ST 626 after the LPS challenge (+5') is able to significantly ($p<0.001$) decrease TNF levels: 1271 pg/ml vs. 7586 pg/ml.

TABLE 5

Effect of ST 626[a] on TNF serum peak levels (1 h post LPS) in LPS-treated[b] mice[c].
Data are expressed as mean values (8 animals) ± S. E..

| Experimental group | Treatment[d] | TNF-α (pg/ml) |
|---|---|---|
| LPS | — | 7586.99 ± 943.49 |
| ST 626 | −60' and +5' | 7.66 ± 127.69* |
| ST 626 | +5' | 1271.06 ± 209.74* |

[a] = The substance was administered orally at the dose of 50 mg/kg either at −60' or again at +5' or only at +5' (with respect to LPS).
[b] = LPS from *E. coli* O26:B6.
[c] = BALB/c mice.
[d] = Time of ST 626 administration with respect to the LPS challenge.
* = Student "t" test (treated vs. LPS): $p < 0.001$.

Evaluation of the effect of ST 626 on serum IL-1β (Interleukin-1 beta) levels induced by LPS in mice.

Animals

Male BALB/c inbred mice (Iffa Credo) aged approx. 8 weeks have been utilized (9 animals per experimental group).

Experimental procedure

The compound ST 626 was administered orally at the dose of 50 mg/kg b.w. following 2 different treatment schedules, namely 1) at −60' and +5', and 2) at +5' and +90' with respect to the LPS injection. The animals were i.p. treated with LPS (from *E. coli* O26:B6), solubilized in sterile saline, at the dose of 10 mg/kg. $CO_2$-anesthetized mice were bled by retro-orbital sinus puncture taking blood samples 4 h following LPS injection, i.e. when IL-1β reached its serum peak levels in mice. Blood samples were all allowed to clot at room temperature for 30' to separate serum, which was then centrifuged (30' at 2000 rpm). The IL-1β serum concentrations were determined by using the commercially available ELISA kit for murine IL-1β (Genzyme, Boston, Mass.) and following the manufacturer's instructions.

Results

Oral treatment with ST 626 (50 mg/kg), administered at −60' and +5' with respect to LPS, dramatically decreases IL-1β concentration to almost undetectable levels (Table 6). Similarly, post-treatment with ST 626 (at +5' and +90' with respect to LPS) is able to significantly ($p<0.001$) reduce IL-1β serum levels.

TABLE 6

Effect of ST 626[a] on IL-1β serum peak levels (4 h post LPS) in LPS-treated[b] mice[c].
Data are expressed as mean values (9 animals) ± S. E..

| Experimenter group | Treatmentd | IL-1β (pg/ml) |
|---|---|---|
| LPS | — | 61.17 ± 9.38 |
| ST 626 | −60'and +5' | 0.06 ± 3.77* |
| ST 626 | +5' and +90' | 12.49 ± 4.14* |

[a] = The substance was administered orally at the dose of 50 mg/kg.
[b] = LPS from *E. coli* O26:B6.
[c] = BALB/c mice.
[d] = Time of ST 626 administration with respect to the LPS challenge.
* = Student "t" test (treated vs. LPS): $p < 0.001$.

Evaluation of the effect of ST 626 on serum IFN-γ (Interferon-gamma) induced by LPS in mice.

Animals

Male BALB/c inbred mice (Iffa Credo) aged approx. 8 weeks have been utilized (8 animals per experimental group).

Experimental procedure

The compound ST 626 was administered orally at the dose of 50 mg/kg b.w. following 2 different treatment schedules, namely 1) at −60' and +5', and 2) at +5', +90' and +180' with respect to the LPS injection. The animals were i.p. treated with LPS (from *E. coli* O26:B6), solubilized in sterile saline, at the dose of 10 mg/kg. $CO_2$-anesthetized mice were bled by retro-orbital sinus puncture, taking blood samples 6 h following LPS injection, i.e. when IFN-γ reached its serum peak levels in mice. Blood samples were all allowed to clot at room temperature for 30' to separate serum, which was then centrifuged (30' at 2000 rpm). The IFN-γ, serum concentrations were determined by using the commercially available ELISA kit for murine IFN-γ (Genzyme, Boston, Mass.) and following the manufacturer's instructions.

Results

Repeated oral treatments with ST 626 provoke a significant decrease (p<0.001) of IFN-γ serum levels, particularly when the compound is administered at −60' and +5' with respect to LPS (461 pg/ml vs 13751 pg/ml) (Table 7).

TABLE 7

Effect of ST 626[a] on IFN-γ serum peak levels (6 h post LPS) in LPS-treated[b] mice[c].
Data are expressed as mean values (9 animals) ± S. E..

| Experimental group | Treatment[d] | IFN-γ (pg/ml) |
|---|---|---|
| LPS | — | 13751.3 ± 1953.5 |
| ST 626 | −60' and +5' | 461.2 ± 58.8* |
| ST 626 | +5', +90' and +180' | 1162.2 ± 238.0* |

[a] = The substance was administered orally at the dose of 50 mg/kg.
[b] = LPS from *E. coli* O26:B6.
[c] = BALB/c mice.
[d] = Time of ST 626 administration with respect to the LPS challenge.
* = Student "t" test (treated vs. LPS): p < 0.001.

Evaluation of the effect of ST 626 on body temperature in mice

Animals

Male BALB/c inbred mice (Iffa Credo) aged approx. 8 weeks have been utilized (8 animals per experimental group).

Experimental procedure

The compound ST 626 was administered orally at the dose of 100 mg/kg b.w. The animal body temperature was recorded by means of a rectal probe both before and 5', 30', 60', and 90' following the compound administration.

Results

Oral ST 626 administration induces a striking reduction of the animal rectal temperature, which is evident as early as 5' after treatment (approx. 1° C.), and reaches a maximum delta (approx. 7° C.) at 60 minutes (Table 8).

TABLE 8

Effect of ST 626[a] on body temperature (°C.) in mice. Data are expressed as mean values (8 animals) ± S. E..

| | Basal | Rectal temperature measurements at: | | | |
| | | 5' | 30' | 60' | 90' |
|---|---|---|---|---|---|
| Mean | 38.21 | 37.18 | 31.90 | 31.38 | 31.86 |
| ± S. E. | 0.14 | 0.16 | 0.13 | 0.31 | 0.37 |
| P | | <0.001 | <0.001 | <0.001 | <0.001 |

[a] = The substance was administered orally at the dose of 100 mg/kg.
Student "t" test (paired data).

Evaluation of the antipyretic and antiinflammatory effects of ST 626 in a phlogosis model induced by Brewers yeast in rats.

Animals

Male Sprague Dawley rats (Iffa Credo) aged approx. 9 weeks were used (6 animals per experimental group).

Experimental procedure

The animals, fasted (no food and no water) 1 hour prior to the start of the test, were administered with 0.25 ml Brewer's yeast suspension (30% in sterile saline) injected into the left hind footpad.

Experiment #1

Four hours and a half after phlogogen injection, one animal group was administered with 50 mg/kg ST 626 in 2 ml of water, while control group only received the same volume of vehicle. A second administration of the compound was given 6.5 h following phlogogen injection. The rectal temperature of each animal was measured at 0, 4.5, 5, 6, 7, and 26 hours following Brewer's yeast injection. Simultaneously with body temperature measurements, oedema of the treated hind paw was monitored. Foot pad volumes were measured plethysmometrically 0, 4.5, 7, and 26 hours after phlogogen injection.

Experiment #2

Two hours and a half after phlogogen injection, one animal group was administered with 10 mg/kg ST 626 in 2 ml of water, while the control group received the same volume of vehicle.

The rectal temperature of each animal was measured at 0, 60, and 120 minutes following phlogogen injection. Additional temperature measurements were taken starting from 10 minutes after the compound administration and went on up to 24 hours.

Experiment #3

Seven days after the end of the experiment #2, a further test was performed on the same animals, re-inducing pyrexia by administering Brewer's yeast as described previously.

Rectal temperature measurements and the volume of the hind footpad (the right one) to be treated with the yeast were determined prior to the inflammatory challenge. ST 626 was administered orally (20 mg/kg) at 1 and 3.5 hours after yeast injection.

Immediately before treatment with ST 626 (1 hour from phlogogen injection) rectal temperature measurements were taken and went on up to seven hours and a half later. Additional measurements were taken after 24 and 31 hours. The outcome of the inflammatory response was monitored by evaluating the volume of the treated footpad by means of a plethysmometer 3.5, 7.5, 24, and 31 after oedema induction.

Results

Oral ST 626 administration at the doses of 10, 20, and 50 mg/kg is able to significantly decrease Breewer's yeast-induced pyrexla, as evaluated by rectal temperature measurements (tables 8–10). Moreover, oedema, developing as a consequence of the treatment with the phlogistic agent, is kept at significantly lower values following treatment with ST 626 (Tables 8 bis and 10 bis).

EXPERIMENT #1

TABLE 8

Effect of ST 626[a] on body temperature (°C.) of rats treated with Brewer's yeast. Data are expressed as mean values (6 animals) ± S. E..

| Time | Control | ST 626 |
|---|---|---|
| 0 | 37.1 ± 0.11 | 37.2 ± 0.13 |
| +4.5 h | 37.8 ± 0.10 | 38.0 ± 0.13 |
| +5 h | 38.1 ± 0.05 | 37.2 ± 0.16▲ |
| +6 h | 38.1 ± 0.08 | 37.4 ± 0.11▲ |
| +7 h | 38.6 ± 0.11 | 36.7 ± 0.15▲ |
| +24 h | 38.2 ± 0.15 | 38.3 ± 0.11 |

[a] = The substance was administered orally. at the dose of 50 mg/kg, 4.5 and 6.5 hours after the phlogogen injection.
Student "t" test: ▲ = p < 0.001.

TABLE 8 bis

Effect of ST 626[a] on hind paw oedema of rats treated with Brewer's yeast. Data are expressed as mean values (6 animals) ± S. E..

| | Mean volume increase (ml) of the treated paw | |
|---|---|---|
| Time | Control | ST 626 |
| +4.5 h | 3.08 ± 0.09 | 3.06 ± 0.06 |
| +7 h | 3.00 ± 0.08 | 2.54 ± 0.11■ |
| +26 h | 3.71 ± 0.09 | 3.60 ± 0.20 |

[a] = The substance was administered orally, at the dose of 50 mg/kg, 4.5 and 6.5 hours after the phlogogen injection.
Student "t" test: ■ = p < 0.01.

EXPERIMENT #2

TABLE 9

Effect of ST 626[a] on body temperature (°C.) of rats treated with Brewer's yeast. Data are expressed as mean values (6 animals) ± S. E..

| Time | Control | ST 626 |
|---|---|---|
| 0 | 36.7 ± 0.10 | 36.5 ± 0.13 |
| +1 h | 37.1 ± 0.07 | 37.3 ± 0.05 |
| +2 h | 37.6 ± 0.08 | 37.7 ± 0.08 |
| +2.7 h | 37.6 ± 0.11 | 37.8 ± 0.13 |
| +3 h | 38.1 ± 0.04 | 37.7 ± 0.06▲ |
| +3.5 h | 38.4 ± 0.08 | 37.7 ± 0.06▲ |
| +4.5 h | 38.8 ± 0.08 | 38.5 ± 0.11♦ |
| +5 h | 39.0 ± 0.03 | 38.7 ± 0.11■ |
| +6 h | 39.1 ± 0.03 | 38.7 ± 0.13♦ |
| +7 h | 39.1 ± 0.05 | 38.9 ± 0.08 |
| +24 h | 37.3 ± 0.10 | 37.5 ± 0.12 |

[a] = The substance was administered orally, at the dose of 50 mg/kg, 2.5 hours after the injection of the phlogistic agent.
Student "t" test: ♦ = p ≤ 0.05; ■ = p ≤ 0.02; ▲ = p ≤ 0.001.

EXPERIMENT #3

TABLE 10

Effect of ST 626[a] on body temperature (°C.) of rats treated with Brewer's yeast. Data are expressed as mean values (6 animals) ± S. E..

| Time | Control | ST 626 |
|---|---|---|
| 0 | 37.07 ± 0.14 | 37.3 ± 0.20 |
| +1 h | 37.4 ± 0.10 | 37.6 ± 0.13 |
| +1.5 h | 37.8 ± 0.15 | 37.6 ± 0.07 |
| +2.5 h | 38.1 ± 0.14 | 37.6 ± 0.20 |

TABLE 10-continued

Effect of ST 626[a] on body temperature (°C.) of rats treated with Brewer's yeast. Data are expressed as mean values (6 animals) ± S. E..

| Time | Control | ST 626 |
|---|---|---|
| +3.5 h | 38.4 ± 0.30 | 38.0 ± 0.20 |
| +4.5 h | 38.7 ± 0.17 | 37.9 ± 0.13● |
| +5.5 h | 38.8 ± 0.08 | 38.2 ± 0.18● |
| +6.5 h | 38.8 ± 0.06 | 38.5 ± 0.08● |
| +7.5 h | 38.7 ± 0.09 | 38.5 ± 0.08 |
| +24 h | 37.8 ± 0.15 | 38.1 ± 0.10 |
| +314 h | 37.3 ± 0.09 | 37.6 ± 0.12 |

[a] = The substance was administered orally, at the dose of 20 mg/kg, 1 and 3.5 hours after the injection of the phlogistic agent.
Student "t" test: ● = p < 0.01.

TABLE 10 bis

Effect of ST 626[a] on hind paw oedema of rats treated with Brewer's yeast. Data are expressed as mean values (6 animals) ± S. E..

| | Mean volume increase (ml) of the treated paw | |
|---|---|---|
| Time | Control | ST 626 |
| +3.5 h | 1.73 ± 0.11 | 1.44 ± 0.04● |
| +7.5 h | 2.05 ± 0.12 | 1.46 ± 0.20● |
| +24 h | 1.90 ± 0.08 | 1.66 ± 0.11 |
| +31 h | 1.90 ± 0.08 | 1.66 ± 0.11■ |

[a] = The substance was administered orally, at the dose of 20 mg/kg, 1 and 3.5 hours after the phlogogen injection.
Student "t" test: ● = p ≤ 0.01: ■ = p ≤ 0.02.

What is claimed is:

1. A therapeutic method for treating septic shock which comprises administering to a patient in need thereof an effective amount of a 6,7-substituted 2-aminotetraline of the formula (I)

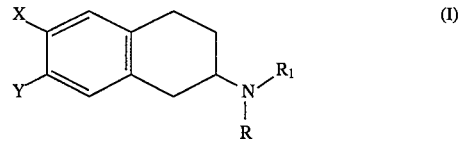

wherein X and Y, equal or different, are selected from the group consisting of methoxy, acetoxy and fluorine and R and $R_1$, equal or different, are selected from the group consisting of hydrogen, ethyl, propyl, cyclopropylmethyl, 2-phenyl-2-hydroxyethyl, 2-hydroxy-2-(4-methylphenyl)ethyl and 2-hydroxy-3-(4-methoxyphenoxy)propyl.

2. A therapeutic method for treating inflammation or reducing fever which comprises administering to a patient in need of an antiinflammatory or antipyretic medicament an effective amount of a 6,7-substituted-2-aminotetraline of the formula (I)

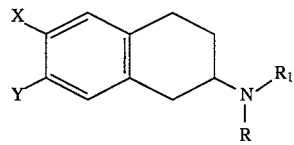

wherein X and Y, equal or different, are selected from the group consisting of methoxy, acetoxy and fluorine and R and $R_1$, equal or different, are selected from the group consisting of hydrogen, ethyl, propyl, cyclopropylmethyl, 2-phenyl-2-hydroxyethyl, 2-hydroxy-2-(4-methylphenyl)ethyl and 2-hydroxy-3-(4-methoxyphenoxy)propyl.

3. The method of claim 1 or 2, wherein the 6,7-substituted 2-aminotetraline is 2-[(N-2-hydroxy-2-(4-methylphenyl)ethyl)amino]-6,7-dimethoxy-tetraline.

4. The method of claim 1 or 2, wherein the 6,7-substituted 2-aminotetraline is 2-[(N-ethyl, N-2-phenyl-2-hydroxyethyl) amino]-6,7-dimethoxytetraline.

5. The method of claim 1 or 2, wherein the 6,7-substituted 2-aminotetraline is 2-[N,N-dicyclopropylmethyl)amino]-6,7-dimethoxytetraline.

6. The method of claim 1 or 2, wherein the 6,7-substituted 2aminotetraline is 2-[N-2-hydroxy-3-(4-methoxyphenoxy)propyl)amino]-6,7-dimethoxy-tetraline.

7. The method of claim 1 or 2, wherein the 6,7-substituted 2-aminotetraline is 2-amino-6-fluoro-7-methoxytetraline.

8. The method of claim 1 or 2, wherein the 6,7-substituted 2-aminotetraline is 2-N-propylamino-6,7-diacetoxytetraline.

* * * * *